United States Patent [19]

Startz, deceased et al.

[11] Patent Number: 4,863,733
[45] Date of Patent: Sep. 5, 1989

[54] METHOD OF PREPARING TREATMENT COMPOSITIONS FOR USE IN PLASTIC OR COSMETIC SURGERY

[76] Inventors: Jack P. Startz, deceased, late of Los Angeles; by Jonathan D. Startz, heir; by Jerry A. Startz, heir; by James A. Startz, heir, all of 10633 Le Conte Ave, Los Angeles, Calif. 90024; by Janet West, heir, 11607 Acama St. #12, Studio City, Calif. 91604

[21] Appl. No.: 770,403

[22] Filed: Aug. 28, 1985

[51] Int. Cl.$^4$ ............................................. A61K 37/02
[52] U.S. Cl. ........................................ 424/101; 14/21; 604/4; 604/5; 604/6; 128/76 B; 128/76 C; 623/8; 623/15
[58] Field of Search ............................. 424/101; 514/21; 604/4-6; 128/76 B, 76 C; 623/8, 15; 530/364, 386, 392

[56] References Cited

U.S. PATENT DOCUMENTS

| | | | |
|---|---|---|---|
| 4,006,220 | 9/1979 | Gottlieb | 424/101 |
| 4,427,651 | 1/1984 | Stroetmann | 514/21 |

FOREIGN PATENT DOCUMENTS

| | | | |
|---|---|---|---|
| 3344656 | 6/1985 | Fed. Rep. of Germany | 514/21 |

OTHER PUBLICATIONS

Remington's Pharmaceutical Sciences "Lidocaine", p. 992, Fifteenth Ed. 1975.

*Primary Examiner*—Ronald W. Griffin
*Assistant Examiner*—Jacqueline M. Stone
*Attorney, Agent, or Firm*—Erik M. Arnhem

[57] ABSTRACT

There are disclosed methods for use in plastic or cosmetic surgery in which a predetermined volume of blood is withdrawn from a donor-patient; and the blood is separated to yield a fraction containing 38% globulins and 54% albumin. This fraction is heated and then reintroduced in conjunction with the respective cosmetic surgery procedures, such as the treatment of scars, breast augmentation, lines near the mouth, in the forehead, and the like. There are also disclosed the corresponding compositions for use in plastic surgery, and these compositions may additionally contain compositions with anesthetic properties and/or coagulants.

4 Claims, 1 Drawing Sheet

TREATMENT METHOD FOR PLASTIC OR COSMETIC SURGERY
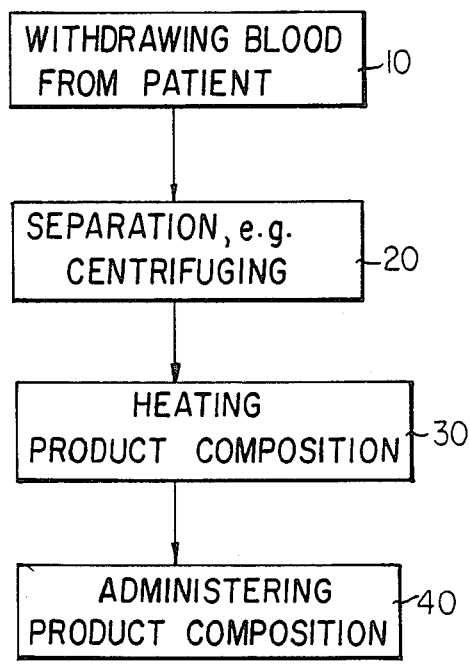

METHOD OF PREPARING TREATMENT COMPOSITIONS FOR USE IN PLASTIC OR COSMETIC SURGERY

BACKGROUND OF THE INVENTION

Field of the Invention

This invention is concerned with treatment methods for plastic or cosmetic surgery, to methods of preparing treatment compositions for use in such surgery, and to compositions for use in plastic or cosmetic surgery.

Recently, considerable interest has been shown in the application of autotransfusion techniques in surgical management for a variety of surgical purposes. Autotransfusion is generally comprised of the steps of removal or salvage of the patient's blood during or prior to the surgical procedure, and re-introduction or administration of the patient's blood, or specific components thereof, to the donor-patient.

Although progress has been made in this field, there has remained the need for specific treatment methods and techniques for use in cosmetic or plastic surgery, to methods of preparing treatment compositions for the use in such surgery, and to specific compositions for use in plastic or cosmetic surgery.

SUMMARY OF THE INVENTION

In accordance with one aspect of the invention, there is contemplated a treatment method for use in plastic or cosmetic surgery which comprises the steps of withdrawing a predetermined volume of blood from a donor-patient; separating the blood in such a way so as to form at least a first upper layer containing in composition 38% globulins and 54% albumin, and a second lower heavy layer of blood cells; discarding the lower layer; treating, for example, heating, the first fraction until it has reached a predetermined viscosity; and administering a therapeutically effective amount of the heated product composition to the donor-patient.

More specifically, in accordance with one aspect of the invention, there is provided a treatment method for use in plastic or cosmetic surgery which comprises the steps of (a) withdrawing a predetermined volume of blood from a donor-patient; (b) separating the blood into a first fraction containing approximately 38% globulins and approximately 54% albumin, and a second fraction containing red blood cells; (c) heating the first fraction until it has attained a predetermined viscosity; and (d) administering a therapeutically effective amount of the heated product composition to the donor-patient.

It is preferred that the method is carried out in such a way that step (d) comprises the application by means of an injection syringe of a therapeutically effective amount of a product composition comprised of at least 38% globulins and 54% of albumin for treatment in conjunction with cosmetic surgery procedures such as the treatment of scars, in breast augmentation or implant procedures, in the treatment of lines near the mouth, in the forehead, and the like.

In accordance with a further aspect of the invention there is also contemplated a process of preparing a composition for use in methods of plastic or cosmetic surgery, comprising the steps of (a) providing a predetermined volume of blood; (b) subjecting the predetermined volume of blood to a separation procedure to yield a product composition containing 38% globulins and 54% albumin; and (c) treating the product composition until it has reached a predetermined viscosity. In this process approximately 2 ounces of blood can be used. It is also preferred that the separation step (b) comprises centrifuging for a period of time sufficient to separate red blood cells from said product composition. Centrifuging may be carried out for a period of time of approximately 15 minutes, or until the desired product composition reports as a first upper layer containing in composition 38% globulins and 54% albumin.

In accordance with another aspect of the invention there is provided a composition for use in conjunction with cosmetic surgery procedures such as the treatment of scars, breast augmentation, lines near the mouth, in the forehead and the like, said composition including at least 38% globulins and 54% albumin. The said globulins can include alpha, beta and gamma globulins.

The compositions of the invention can also include a therapeutically effective amount of a compound having the capability to serve as a local anesthetic, e.g. Xylocaine which may be used in the form of 2% Xylocaine.

The composition can additionally include a therapeutically effective amount of a coagulant, e.g. sodium citrate, which may be present in amounts of from approximately 0.5 to approximately 4.0 cc.

In accordance with a further aspect of the invention there is provided an implant material for use in plastic or cosmetic surgery techniques, which implant material includes at least 38% globulins and 54% albumin.

Included in the objects of this invention are:

To provide treatment methods for plastic or cosmetic surgery which allow easy withdrawal of blood from the donor-patients and using portions of the patient's own blood in conjunction with the surgical procedure.

To provide simple yet effective methods of treating plastic or cosmetic surgery patients by autotransfusion techniques whereby the blood is withdrawn from a patient and portions of the patient's own blood are re-used in conjunction with the surgical procedure.

To provide therapeutically effective compositions for use in conjunction with cosmetic, plastic and the like surgery procedures such as the treatment of scars, breast augmentation or implantation, treatment of lines near the mouth, in the forehead, and the like.

BRIEF DESCRIPTION OF THE DRAWING

The above and other objects, features and advantages will become apparent from the following description, reference being made to the accompanying drawing, in which the single FIGURE is a schematic flow diagram of the several steps contemplated in accordance with one aspect of the method of this invention.

SPECIFIC DESCRIPTION

In general terms, the method diagrammatically indicated in the sole FIGURE, is applicable in the treating of cosmetic or plastic surgery patients, and firstly comprises the step of: withdrawing (10) a predetermined volume of blood from the patient, i.e. donor-patient. It is preferred that approximately 2 ounces of blood are drawn from a patient by means of a syringe. This withdrawal can be carried out according to the conventional method of withdrawing blood from the arm of a patient, with a tourniquet being applied as is customary. The volume or amount of blood that is being withdrawn is then evacuated into a test tube or vacutainer, i.e. a sterile tube, vacuum tube, or similar receptacle.

Next, the withdrawn blood is subjected to centrifuging (20), or a similar separation procedure, in a centrifuge, for a period of time sufficient to separate the blood. Thus, upon spinning for 15 minutes in the centrifuge, the material is separated to yield, in the pertaining vessel or container, a first upper layer containing in composition 38% globulins and 54% albumin. This layer is amber in color. There is also formed a second, lower heavy layer comprised of red blood cells, and this lower layer can be discarded.

The product composition is treated, e.g. heated (30) to attain a predetermined viscosity, with heating being carried for 4 to 8 minutes at 215° F.

It was found that administering (40) a therapeutically effective amount of the heated product composition having a heavy viscosity is beneficial for patients with superficial lines. A lighter viscosity is preferred for deeper penetration, e.g. breast augmentation or implantation.

The application is preferably carried out by inserting a cartridge, containing the product composition with at least 38% globulins and at least 54% albumin, into an injection gun for administering the selected amount to the patient, i.e. donor-patient.

The treatment method for plastic surgery may also include the inclusion of a predetermined amount of additives, either at the time of withdrawing the blood from the patient, or in a subsequent step. Thus, it may be carried out by use of a plastic syringe, say having a volume of 20 cc, which contains 6 cc sodium citrate, and which is then drawn to 15 cc. Instead of sodium citrate, one may also use acid sodium citrate, at times referred to as disodium citrate, disodium hydrogen citrate, and alkacitron, and this may be preferred because of its known properties as an anticoagulant to prevent clotting of blood intended for transfusion. It may be preferable to sodium citrate because it prevents carmelization of glucose on sterilization because of its acidity.

In general terms it may be said that the method also includes the provision of a suitable coagulant.

Thus, the invention contemplates the provision of an effective and simple method of treating by autotransfusion techniques the blood withdrawn from a patient and re-using portions of the patient's own blood in conjunction with the surgery.

There are also contemplated therapeutically effective compositions for use in conjunction with cosmetic surgery procedures such as the treatment of scars, breast augmentation or implantation, treatment of lines near the mouth, in the forehead, and the like, and which are treated either with or without a coagulant in accordance with the details described above.

There are further contemplated therapeutically effective compositions for use in conjunction with cosmetic surgery procedures, which compositions also include substances having local anesthetic properties, such as Xylocaine [Lidocaine. 2-(Diethylamino)-N-(2,6-dimethylphenyl)acetamide; $C_{14}H_{22}N_2O$], and the like compositions.

The bioplast composition may include the components enumerated in the following:

TABLE

| No. | BIOPLAST COMPOSITIONS |
|---|---|
| 1 | 0.5 cc 3.8% sodium citrate - 4.5 cc blood (plain or coagulated) |
| 2 | 1.0 cc 3.8% sodium citrate - 4.5 cc blood |

TABLE-continued

| No. | BIOPLAST COMPOSITIONS |
|---|---|
| 3 | 1.5 cc 3.8% sodium citrate - 4.5 cc blood |
| 4 | 2.0 cc 3.8% sodium citrate - 4.5 cc blood |
| 5 | 3.0 cc 3.8% sodium citrate - 4.5 cc blood |
| 6 | fibroplast (bioplast) with Xylocaine 6.0 cc 3.8% sodium citrate - 9 cc blood 9.2 cc serum + 0.8 cc 2% Xylocaine plain |
| 7 | same as 6 but coagulated |

The preferred bioplast solution is No. 1, plain or coagulated, depending on the defect to be corrected. In this dilution, no Xylocaine is necessary. In higher concentrations, sodium citrate stings, and Xylocaine 2% plain is added for the comfort of the patient.

It is also preferred that the coagulation is carried out at 250° F. for 4 to 6 minutes in a carpule (1.8 cc).

Coagulation of the product composition was readily achieved by filling sterile carpules with serum and baking in a toaster oven. On the other hand, there may remain the need to develop a fully consistent method of coagulation, and perhaps it may be more appropriate to use a water bath under certain circumstances.

The centrifuging time is usually of from 15 to 20 minutes, at 22 on the speed control of the apparatus.

It is currently envisaged that the composition containing 38% globulins and 54% albumin is a highly suitable implant material for humans or animals.

The product composition may be used heated or not heated, depending on the applications. Coagulation should be carried out when it is contemplated that the body area subjected to cosmetic improvement is like a pit, e.g. acne scars. A scar area need no coagulation of the product composition. When the area is to be elevated, the product composition should be heated.

Improvement of the treated area is almost immediate, although in certain cases, a second application may be administered within approximately two weeks. The effect appears to be lasting.

For breast implantation heating of the product composition is generally not necessary.

A scar area that is reddish loses its color to some extent.

Specific application details and the results are indicated in the following:

EXAMPLE 1

This patient had facial scars from acne. A chemical peel was performed, and so were bioplast injections. The patient is greatly improved and very happy with the results.

EXAMPLE 2

This patient had deep nasal-labial lines and mid-third facial depressions. Over a six month period 8 treatments were given. The contour of the face is much softer and prettier. The patient is very happy with the treatments.

EXAMPLE 3

This patient had scars on the left, posterior surface of the thigh and buttock from orthopedic surgery. Injections into the scar flattened it and reduced the redness. The soft tissue defect created by the orthopedic surgery was filled in. Fat extraction surgery was performed one month prior to this time to contour the thigh. The patient is very happy with the results.

EXAMPLE 4

This patient's breasts were small with slight ptosis. Both breasts were injected twice. There was a two-week interval between treatments. There is excellent improvement in both lift and contour, and the patient is very happy with the results.

EXAMPLE 5

Rhinoplasty

This patient had a rhinoplasty. Some irregularities in healing were corrected by injecting product No. 5 with Xylocaine to the columella to straighten and raise the nasal tip, to the dorsum for a ltump (takeaway) and to the left nostril to widen and match the right nostril. This application prevented a full surgical procedure.

EXAMPLE 6

This patient had a traumatic scar of the forehead which was injected with product No. 5 with Xylocaine. The patient is greatly improved and very pleased with the result.

EXAMPLE 7

This patient had a drooping nasal tip. She had a rhinoplasty, nares procedure (to reduce flare of nostrils) and a surgical revision of her nasal tip. She was injected with product No. 2 in her nasal tip and columella and subsequently with product No. 4. She is pleased with the improvement.

While the invention has been described and illustrated with respect to preferred embodiments, it is not intended to restrict the scope of the appended claims, which themselves recite those features regarded as essential to the invention.

It is claimed:

1. The method of preparing a composition useful in treatment procedures of the type including plastic surgery and cosmetic surgery wherein a predetermined volume of blood to serve as the source material for the composition is withdrawn from a donor-patient and the composition is administered to that donor-patient, said method comprising:
   separating by centrifuging the withdrawn blood into a first fraction containing 38 volume percent of globulin and 54 volume percent of albumin, and into a second fraction containing blood cells; and
   heating said first fraction at a temperature from the range of from about 215° F. to about 250° F.

2. The method of claim 1 wherein said separating step is carried out from a period of time of approximately 15 minutes.

3. The method of claim 1 wherein said heating step is carried out for a period of time of approximately 4 to 15 minutes.

4. The method of claim 1 wherein approximately 2 ounces of blood are withdrawn.

* * * * *